United States Patent [19]

Hotham

[11] 4,095,775
[45] Jun. 20, 1978

[54] PARTICLE EVALUATOR

[76] Inventor: Geoffrey A. Hotham, 1130 Channel Dr., Santa Barbara, Calif. 93108

[21] Appl. No.: 642,915

[22] Filed: Dec. 22, 1975

[51] Int. Cl.² ............... G01N 21/00; G01N 21/18; G02B 21/34
[52] U.S. Cl. ............................... 356/102; 356/181; 250/574; 350/95
[58] Field of Search ............. 356/102, 103, 246, 181; 250/574; 350/63, 89, 95

[56] References Cited

U.S. PATENT DOCUMENTS

| | | | |
|---|---|---|---|
| 3,609,043 | 9/1971 | Simmons et al. | 356/102 |
| 3,614,231 | 10/1971 | Sharn | 356/102 |
| 3,646,352 | 2/1972 | Bol et al. | 356/102 |
| 3,720,470 | 3/1973 | Berkham | 356/103 |

Primary Examiner—Conrad J. Clark
Attorney, Agent, or Firm—Reed C. Lawlor

[57] ABSTRACT

The invention is employed for evaluating particles, such as droplets of aerosol sprays suspended in a gaseous medium. A stream of the particles to be analyzed is flowed into a narrow sample zone across the optical axis of a beam of light. Scattered radiation from the particles is focused on the image plane in which a photosensitive surface is located. Images of particles formed there are reproduced on a fluorescent or phosphorescent display screen of a cathode ray tube. A scale on the screen is employed for measuring the dimensions of the particles. The confinement of the stream of the mixture to about the depth of focus of the objective lens of the camera reduces effects of out-of-focus particles and permits evaluation of individual particles.

21 Claims, 7 Drawing Figures

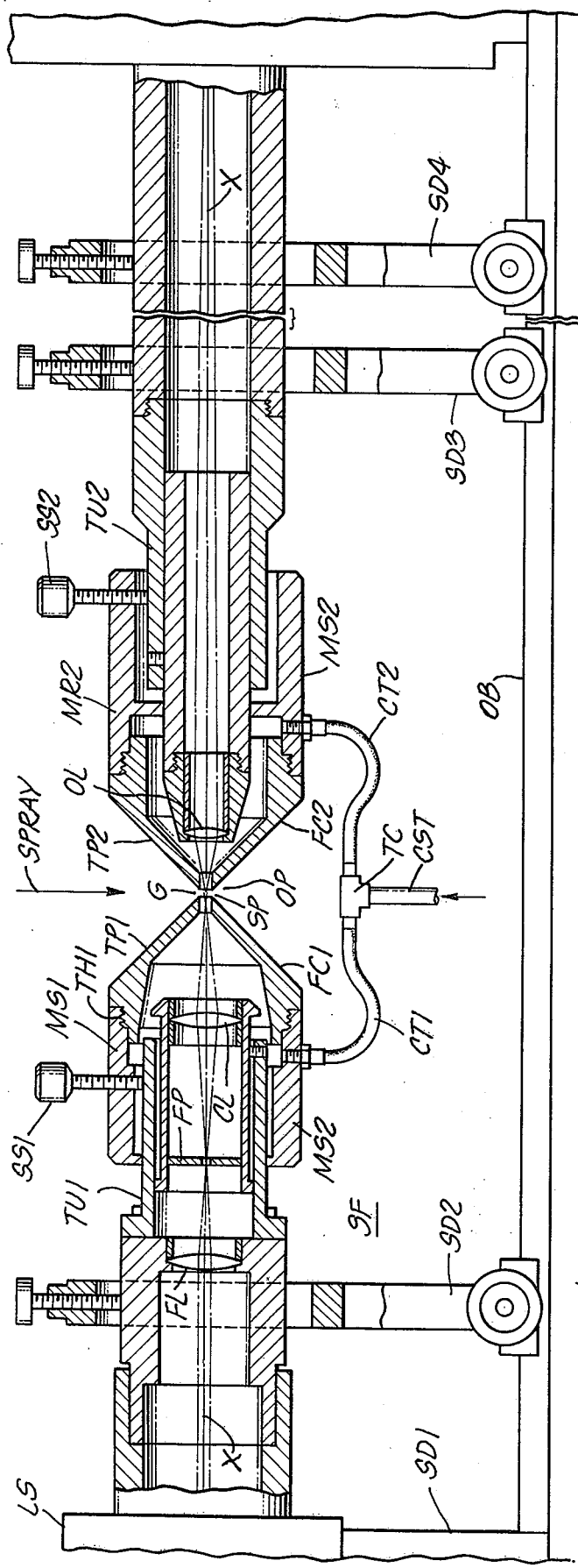

PARTICLE EVALUATOR

This invention is concerned with an improved system for evaluating particles and has particular application to the measurement of the sizes of such particles, especially liquid aerosol particles that originate in aerosol sprays.

While the invention may be employed particularly for the measurement of the sizes of droplets, it may also be employed to study solid particles such as asbestos particles and coal dust. It may also be employed in the study of impaction, evaporation, agglomeration, and droplet disintegration. For simplicity of explanation, the invention will be described particularly with reference to the measurement of the sizes of such liquid aerosol particles suspended in air.

The importance of this invention resides particularly in the fact that aerosol sprays are developed in many circumstances where the inhalation of the spray is dangerous to the user. This applies, for example, to deodorant sprays, hair sprays, paint sprays, air fresheners, insecticides, and the like, where the spray is likely to be inhaled by the user. Such a spray is usually dispensed by releasing it through a nozzle from a pressurized container by depressing a simple valve that normally blocks the passage through the nozzle when the valve is not depressed.

In the design of such spray nozzles, it is important to design the nozzle in such a way that the particles or droplets formed in the spray are neither excessively large nor excessively small. If they are too large, such as in excess of 1000 micrometers in diameter, the spray tends to deposit on the skin or other object being sprayed as a flowable liquid. If they are too small, such as below about 10 micrometers in diameter, they are easily inhaled into and retained in the lungs, where they may prove to be toxic.

When applied to particle size measurement the invention relates particularly to a system in which optical images of the particles to be studied are recorded on magnetic tape or on film, or the like, and the recordings are then reproduced as optical images and then sized by making measurements directly on the optical images of the particles. When applied to other methods of evaluating particles the recordings are reproduced as optical images and then studied visually or otherwise.

While many systems have been developed for measuring particle size, this invention is advantageous because of the fact that sharp optical images of the particles are formed, and fogging of such images is reduced by confining the sample of the gas containing the particles to a very short space along the axis of a light beam within the confines of about the depth of focus of an optical system that forms an optical image of particles on an image recording medium.

In one prior art system, somewhat similar to the present system, "holographic" images are formed on film and then these holographic images are reproduced by a holographic reproducing system. Such a system is referred to in an article by W. W. Zinky appearing in Annals NY-ACAD-SCI 158:781-52 (1969) titled "Hologram Techniques for Particle Size Analysis".

In a somewhat similar system such as that disclosed in Silverman et al, U.S. Pat. No. 3,451,755, a record is made of the diffraction patterns produced by the particles and measurements are made on the diffraction patterns in order to calculate the sizes of the particles.

Numerous other methods having a superficial resemblance to the present invention, involve transmitting light from a detected particle to a photodetector such as a photoelectric or photomultiplier tube. Such systems are disclosed in Solkowski et al U.S. Pat. No. 3,504,183, Goldberg U.S. Pat. No. 3,536,898, Shaw U.S. Pat. No. 3,614,231, and Bol et al U.S. Pat. No. 3,646,352. In such systems, the diminution in the amount of light reaching the photodetector, when a particle enters the light beam, causes the photodetector to produce a pulse of electric current. Such systems suffer from the disadvantage that they are incapable of distinguishing between several particles that lie within the field of view of the optical system at any one time and a single large particle that lies in the field of view at another time.

Of the prior art now known to me, only the Simmons et al U.S. Pat. No. 3,609,043 involves the formation of an image of particles on an image recording system as in a vidicon system.

Such a system is also described in my article titled "Sizing Aerosols in Real Time by Pulsing UV Laser Machine" which appears as National Bureau of Standards Special Publication 412 under date of May 7, 1974 and which was issued in October 1974. I have employed such a system for over a year. Both the Simmons et al system and my prior system suffer from the disadvantage that out-of-focus particles that may be present produce images that interfere with sharp imaging of the in-focus particles. Sometimes in such systems, programmed computers are employed to discriminate between particles to be studied and other particles that might interfere with such study.

In one form of the best mode of practicing this invention now contemplated, a vidicon camera is aligned with a laser-beam source along a common optical axis, and the optical axis is entirely enclosed within a light tunnel that extends from the light source to the screen of the vidicon camera except for a narrow sampling gap between the ends thereof. In another form of the best mode of practicing this invention now contemplated, the vidicon camera tube is oriented with its axis on a line which is normal to the optical axis of the laser-beam source while the lens of the vidicon camera lies on that common optical axis, and an apertured mirror is located on the optical axis in a plane at 45° to the optical axis. An aperture in the mirror is located at the point where the laser beam is focused to provide for spatial suppression of the laser beam, but reflection of the radiation scattered by the droplets to a focal plane at the face of the vidicon camera. In an alternative arrangement for separating the rays of the laser beam from the scattered radiation, the laser beam is deflected by a small mirror to the side of the optical axis and the scattered radiation is transmitted directly to the vidicon camera tube along the optical axis.

In either form the particles to be evaluated or sized are projected into the sample zone along a path that is transverse to the optical axis X—X.

IN THE DRAWINGS

FIG. 1 is the schematic diagram of the invention;

FIG. 2, FIG. 2A, and FIG. 2B are diagrams representing arrangements for confining the low of a gas sample into the focal region of the objective system to a narrow zone along the optical axis;

FIG. 3 is a cross-sectional view of the particle size measuring system taken along the optical axis and showing some features of construction in more detail;

FIG. 4 is a diagram employed to explain how the lens of different focal lengths and magnification characteristics are located relative to the crossover point of the laser beam; and FIG. 5 is a diagram employed to explain a second form of the invention.

Figure 1:
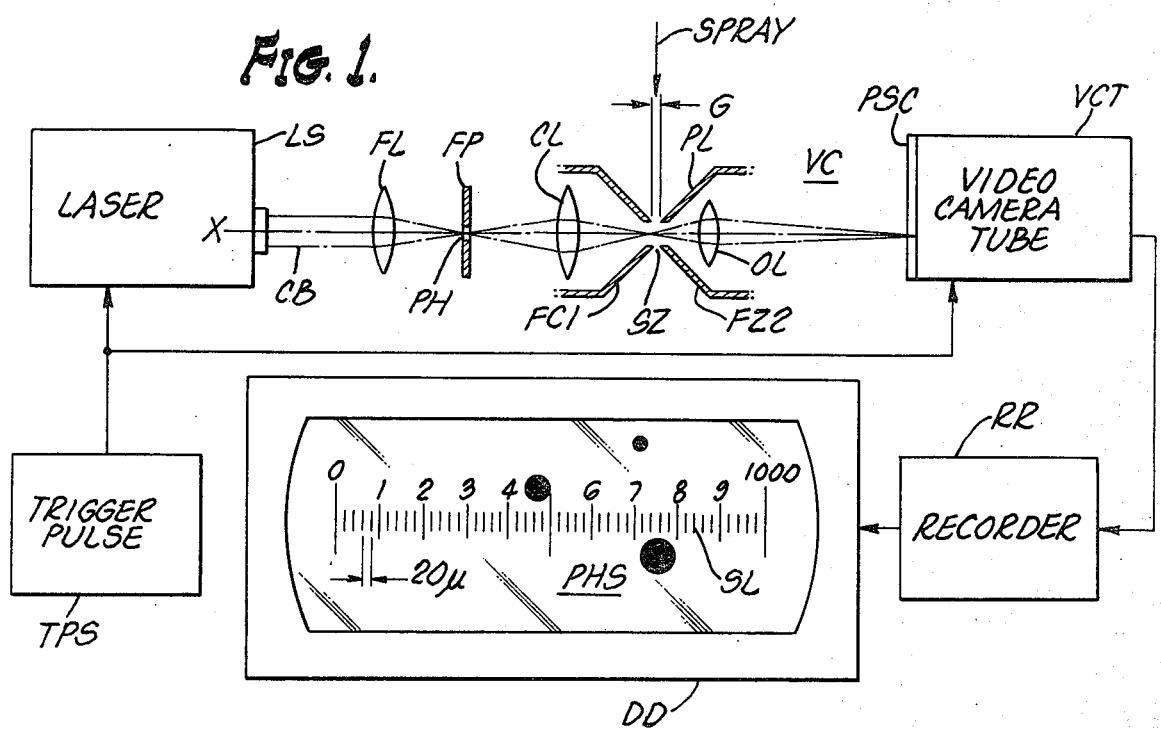

As indicated in the drawings, particularly FIGS. 1 and 3, the embodiment of the present invention shown there, employs a broad-beam laser with its optical axis coincident with the optical axis of a vidicon or video camera employing an objective lens OL and a vidicon camera tube VCT. A restrictor comprising two focal cones FC1 and FC2 is employed to confine the flow of an aerosol-bearing gas to a narrow sample zone which is focused on the screen PSC of the vidicon camera tube VCT by means of the objective lens OL.

The vidicon camera tube VCT has associated with it conventional means for scanning the screen to produce a stream of electrical signals that have amplitudes corresponding to the intensity of light impinging upon various points of the photosensitive screen PSC. These signals are recorded in a magnetic tape recorder RR of conventional type employed with a video camera tube and these signals may be played back or reproduced to produce a visible optical image on the fluorescent or phosphorescent screen PHS of a cathode ray tube forming a display device DD.

It is to be noted in FIG. 1 that the face of the display device DD is provided with a scale to assist in measuring dimensions of droplets appearing in the image displayed. One way to produce such a scale accurately is to position a marked transparent reticule in the object plane of the object lens OL in the sample zone SZ with the scale arranged in a plane transverse to the optical axis X—X and to play back an image of that scale on the video camera tube and then to mark the screen in accordance with the positions of the lines in the displayed image of the reticule.

A trigger pulse source TPS synchronizes the energization of the laser with the operation of the video camera VC so that the sample in the sample zone SZ is illuminated instantaneously, that is for a very short time interval, such as about 10 nanoseconds, while the sample zone is being recorded or sensed by the vidicon camera. As mentioned above, the image formed on the screen PSC of the vidicon camera is recorded on a magnetic tape recorder RR.

With this invention, images of droplets that are exposed to light from the laser source LS are displayed as sharp images on the screen and the dimensions of individual droplets may be estimated by means of the scale.

The invention involves confining the stream of particles under study substantially entirely to a narrow zone SZ that intercepts the beam of radiation from the laser source and then the focusing of radiation scattered by droplets as separate sharp images on the screen PSC.

The length of the sample zone along the optical axis X—X approximates the depth of focus of the objective lens OL. The depth of focus of the vidicon camera at the object plane is given by the following equation:

$$(\lambda/NA^2)$$

where $\lambda$ = wavelength and $NA$ = numerical aperture of the lens.

For an objective lens having a focal length of 4 inches and a numerical aperture of 0.03 and positioned to operate with a magnification of 10X, as described hereinafter, the depth of focus is 333 micrometers.

By restricting the flow of the sample under study substantially entirely to a narrow region at a sample plane that is conjugate relative to the photosensitive screen PSC, more accurate measurements of particle size are attainable than otherwise.

The trigger pulse source TPS may be of the kind in which a single laser pulse is generated under manual control of the operator, or of the kind in which laser pulses are generated at uniform intervals so as to make a series of video photographs or "pictures" of the sample as the sample flows through the sample space. In practice the velocity of the particles transverse to the optical axis X—X usually lies in a range from a few micrometers per second up to several hundred meters per second. The device may be used to observe substantially stationary particles also.

The laser-beam source LS may be in the form of a nitrogen laser, model N2-50, manufactured by Laser Energy, Inc. of Rochester, N.Y., combined with a laser-beam expander, model 1526, manufactured by Oriel Corporation of America, Stamford, Conn., which is employed as a spatial filter. The laser source generates a collimated beam CB of monochromatic radiation having a wavelength of 0.337 micrometers and having a diameter of 3 millimeters. In this arrangement a filter lens FL causes this beam to converge onto a plate FP having a pinhole PH in it of a diameter of 0.10 micrometers. The term filter is employed here to describe a spatial filter which is formed by the combination of the lens FL and the pinhole plate FP. Employment of a laser-beam source with an expander and spatial filter makes it possible to provide a field of nearly uniform intensity over the area of the photosensitive screen PSC. Under some circumstances that spatial may be omitted and the beam, which is normally only 3 millimeters in diameter, may be utilized without condensing.

Figures 2A, 2B:
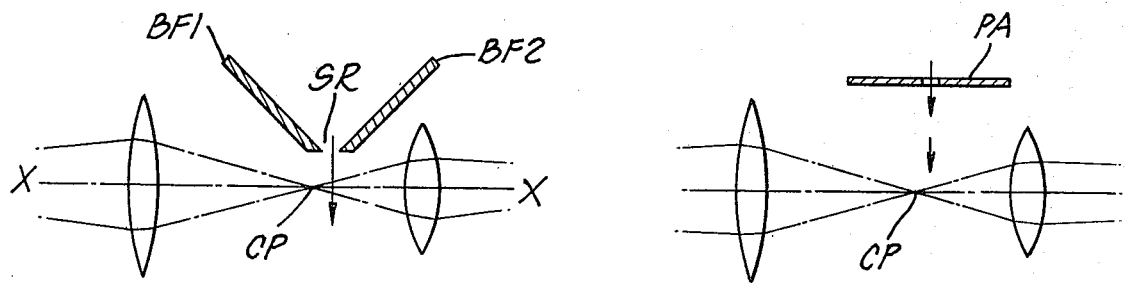
Figure 2:
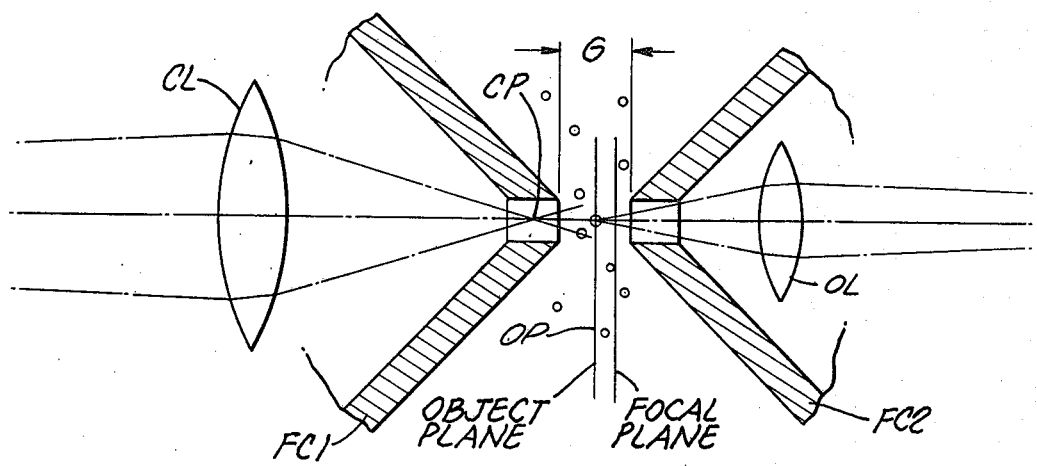

In order to attain maximum intensity of the image on the video screen, a condenser lens CL is employed for focusing an image of the pinhole PH at a crossover point CP on the upbeam side of the sample zone. The crossover point CP of the condensing system is spaced from the object plane OP, so that in the absence of particles the monochromatic radiation illuminates the entire area of the photosensitive screen PSC substantially uniformly. Though the crossover point of illumination beam may be located on either side of the object plane, light transmission efficiency is maximized by locating it on the upbeam side as illustrated In FIG. 2. It is to be noted that the crossover point CP is imaged at a point between the objective lens OL and the video screen PSC so that the monochromatic radiation is spread over the entire area of the video screen PSC.

It will be understood that the radiation diverges from the condensation point CP. The two focal cones are located at positions suitable for transmitting substantially the entire condensed beam to the video screen PSC. A sample zone is thus employed that has an area that is evenly illuminated by the monochromatic radiation without, however, cutting off any substantial part of that radiation by interception of the radiation between the cone apertures.

The restrictor found most satisfactory for use in this invention comprises a pair of focus cones FC1 and FC2 that encircle the optical axis, X—X and have small apertures at their tips which are located close together to form a narrow gap G through which the sample is flowed transversely.

A camera or objective lens OL focuses an image of any particles in the gap onto the photosensitive screen PSC. The camera lens is located much more closely to the gap G than to the photosensitive screen PSC, thus providing high magnification and in effect providing a microscopic view of the sample space. In effect, the camera lens OL acts as an objective lens of a video microscope.

In FIG. 4 there are illustrated arrangements for properly locating lens L1 or lens L2 where lens L1 has a focal length of 4 inches and is operated with a magnification of 9X and lens L2 has a focal length of ½ inch and is operated with a magnification of 90X. In either event, the lens is located at a position relative to the sample zone SZ such that the sample zone forms an image on the window of the video camera tube VCT which is slightly larger than the window. Such a window normally has a height of ⅝ inch and a width of ¾ inch. To achieve this result the object plane OP intersects the diverging beam DB at such a position that the area of the intersection of the object plane is magnified to produce an image of the required size on the screen PSC of the video camera tube. Thus, as illustrated in FIG. 4, it will be noted that lens L1 is located farther from the crossover point CP than the lens L2. Furthermore, it is to be noted that the object plane corresponding to lens L1 is located farther from the crossover point that the object plane OP2 of the lens L2. The cones are positioned accordingly to confine the sample zone to a region close to the corresponding object plane.

A unit in which the invention has been implemented is shown in more detail in FIG. 3. As indicated there the optical axis X—X of the system is enclosed in a light-proof, gas-leak-proof tunnel except for a narrow sampling gap G, and the focal cones FC1 and FC2 are adjustably mounted on tubular members TU1 and TU2 to facilitate relative movement of the apertured tips TP1 and TP2, for the dual purpose of adjusting the tips relative to the objective plane of the camera lens OL and to adjust the location of the image of the pinhole relative to the objective plane OP.

To facilitate precise adjustment the laser source together with the spatial filter SF are supported by standards SD1 and SD2 which are clamped upright on the tracks of an optical bench OB, with the entrance tube TU1 extending toward the sample zone SZ. Likewise, the exit tube TU2 which supports the camera lens OL in fixed position relative to the face of the video camera VC, is supported on the optical bench OB by means of standards SD3 and SD4 which are clamped onto the optical bench OB. Suitable mounting rings are employed to hold the filter lens FL, the filter plate FP, and the condenser lens CL in adjustable but normally fixed relative positions within the entrance tube TU1 of the light source.

The first focal cone FC1 is attached to a mounting sleeve MS1 which encircles the tube TU1 and is locked in place thereon by means of setting screws SS1. Threaded parts TH1 permit adjustment of the first cone FC1 relative to the condensing lens CL.

The second focal cone FC2 is attached to a mounting sleeve MS2 which encircles the tube TU2 and is locked in place thereon by means of setting screws SS2. Threaded parts TH2 permit adjustment of the second cone FC2 relative to the first cone FC1.

In practice coarse adjustment of the gap may be made by movement of the standards SD1 and SD2 or the standards SD3 or SD4 along the length of the optical bench or by adjustment of the mounting sleeves MS1 or MS2 along the lengths of the tubes TU1 and TU2, respectively. And then fine adjustment of the gap may be made by rotation of the cones FC1 and FC2 relative to the mounting sleeves MS1 and MS2.

Two capillary hoses CT1 and CT2 are connected to lateral openings in the mounting sleeve MS1 and MS2 in order to admit air or other gas under pressure to the space within the interior of the focal cones FC1 and FC2. Air or other gas under pressure is supplied to these capillary hoses CT1 and CT2 from a common supply tube CST that is connected to them at a T-connector TC. Gas supplied under pressure to the interior of the cones flows gently toward their tips and into the gap thereby opposing the flow of particles from the sample into the interior of the tunnel, thus helping to confine the flow of sample gas to the gap G between the tips TP1 and TP2 of the cones FC1 and FC2. At the same time the flow of the gas supplied under pressure is maintained sufficiently low so that it will not interfere substantially with the flow of the spray through the gap from one side of the optical axis to the other.

In practice the thickness of the gap, that is its length, along the optical axis, is set between about 0.010 inch and about 0.100 inch, thus limiting the gap to a thickness approximating the depth of focus of the camera lens OL.

In an embodiment of the invention that has proved satisfactory, the focal length of the camera lens was 1 inch and the focal length of the condensing lens CL was 1 inch. The camera lens OL was located approximately 40 inches from the photosensitive screen PSC.

The object plane OP of the camera lens OL is conjugate with respect to the photosensitive screen PSC and the focal cones FC1 and FC2 are located on opposite sides thereof.

In this case the aperture of the camera lens OL was approximately 0.125 inch so that the value of the numerical aperture NA of the lens was about 0.125.

In the arrangement shown in FIG. 3 the image of the pinhole PH is focused in a plane that is displaced in the upbeam direction from the object plane OP, in practice being located on the light source LS side of the optical plane and within the tip TP1 of the upbeam focal cone FC1. Thus, the image of the pinhole is slightly out-of-focus in the sample zone, and illuminates various parts of the sample zone more or less uniformly. It is better to focus the image of the pinhole on the upbeam side of the sample zone rather than on the downbeam side in the interest of efficiency and in order to avoid loss of light by interception of the converging beam by the upbeam cone CP.

The invention also may be practiced by employing a convex lens in place of the condenser lens CL and locating its upbeam focal point at the pinhole PH so that the laser beam traveling to the focal cone is a collimated beam. Such an arrangement is particularly useful when the beam expander is omitted and the diameter of the orifices of the focal cones FC1 and FC2 approximate the diameter of the beam. In this case again, the laser beam is arranged to be out-of-focus on the photosensitive screen PSC and to cover the face of the window of the screen to provide even illumination.

In another arrangement, lens FL, pinhole FP, and lens CL are omitted. Raw collimated laser light from the illumination source is used directly to illuminate the spray particles.

In any event, since the droplets are in effect opaque in the system described above, black images of the droplets are formed at the image plane against a substantially uniform background of monochromatic light.

The focal cones and their mounting sleeve are composed of a firm plastic material, such as Delerin, that is manufactured by Du Pont Co., Wilmington, Del. The remaining parts of the tunnel walls, including the tubular members TU1 and TU2 are generally metal. The orifices at the tips of the cones have a diameter of about 1 to 2 millimeters. The interior surfaces of the focal cones, the mounting sleeves, and the tunnel walls are made black such as by painting so as to reduce effects of stray light.

The cones have half angles between the conical surfaces of about 45° and more particularly between about 30° and 60°. Such cone shape avoids a loss of light that might otherwise occur if the cones tapered less and at the same time prevents bouncing or splashing of particles from the exterior cone surfaces into the sample zone.

In the study of the spray which includes large droplets having diameters of 1000 micrometers, the gap is made as much as 0.5 to 1.5 millimeters thick. For smaller droplets having diameters in the order of 5 micrometers, the gap spacing is made much smaller and of the order of about 100 to 300 micrometers.

The focal cones FC1 and FC2 serve not only to restrict the sample space because of the narrow gap, but also to restrict the sample under study to the region of the gap so that droplets do not fall upon the surfaces of the lenses, such as the camera lens OL and the condenser lens CL. Further restriction of the sample to the gap is aided by flowing gas gently from the interior of the light tunnel into the gap. While a Venturi effect caused by the flow of a stream of a sample through the gap tends to reduce the pressure of gas in the gap and thus to impede the flow of the particles of the sample stream into the space inside of the cones, the application of a small positive pressure to the gas within the cones is even more effective in confining the flow of the droplets under study through the gap.

By confining the droplets to a narrow zone in the gap, the only droplets that are photographed by the video camera, are in sharp focus, thus avoiding the obscuring of the dimensions of the in-focus droplets because of the fog or mist that might otherwise form in the downbeam cone or condense on the objective lens OL.

While the invention is practiced in the best mode by means of an optical tunnel employing two adjacent cones with orifices at their tips, as described, above, the invention may also be practiced by spraying the sample into the sample zone through a slit formed between the edges of two baffle plates BF1 and BF2 as indicated in FIG. 2A, or through a narrow slit in a flat plate PA as indicated in FIG. 2B. Of these two restrictions, the one employing two baffle plates BF1 and BF2 is superior because the slit SR may be located adjacent the optical axis X—X and directly opposite the sample region.

The cones are made very small so that they also may be positioned very close or adjacent to the optical axis. Such cones tend to splatter the spray into the measuring zone less than baffles. Cones allow spray particles to pass over them and the particles are not so easily deflected into the measuring gap.

In still another way of confining the test sample to a narrow zone the sample is injected across the optical axis X—X through a device which encloses the test sample within a sheath of clean neutral gas. Systems for supplying gas within such a sheath are well known. One is shown, for example, in Salkowski et al U.S. Pat. No. 3,504,183.

In an alternative form of the invention illustrated in FIG. 5, a spatial filter in the form of an apertured mirror AM oriented at 45° relative to the optical axis X—X, is employed to separated the scattered radiation from the original unscattered laser beam. As there indicated, the original laser radiation represented by the dashed lines DL is brought to a focus at an aperture AP at the center of the mirror on the downbeam side of the objective lens OL and is transmitted through the mirror. The scattered radiation represented by the nearly solid lines SL are reflected by the mirror AM to the face of the video camera tube VCT. This arrangement provides an image at the photosensitive screen PSC of the kind formed by a dark field microscope. This arrangement has the advantage over that described in detail above in that the area of the droplets is bright and the background is dark thus loading the electronic amplifier of the video camera tube to a lesser extent. For optimum effect, the aperture is elliptical and its projection onto a plane perpendicular to the optical axis is circular.

If desired, an alternative arrangement may be employed that is complementary to that just described. In the alternative complementary arrangement, a small elliptical mirror is located at the downbeam focal point of the laser beam and the video camera tube is located on the same axis X—X as the laser source, as shown in FIG. 3. In the latter case, the spatial filtering involves deflecting the laser beam from the photosensitive screen, whereas in the former case the spatial filtering involves deflecting the scattered radiation to the photosensitive screen.

In this specification, the terms "upbeam" and "downbeam" are analogous to the terms "upstream" and "downstream", the light beam, in effect, constituting the stream referred to. For example, the term "upbeam" has been employed to refer to positions that are to the left of the sample zone as shown, for example, in FIG. 1 and hence are relatively closer to the source LFS and the term "downbeam" has been employed to refer to positions that are to the right of the sample zone and hence are relatively closer to the video camera tube VCT.

While the invention has been described with particular reference to the sizing of droplets that are sprayed through the gap from one side thereof to the other, the invention may be employed in many other ways. For example, in some cases, a strand of hair of a spider-web, or other impaction target, strand may be located in the gap and a study may be made of either the impaction of spray onto such strand or of the evaporation of condensate therefrom, or of deposits formed thereon. The invention is also applicable to the evaluation of particles that are suspended in a liquid and may even be employed to evaluate particles which are projected through the gap in a vacuum or otherwise. The invention is not limited solely to measurement of sizes and changes in size of particle, but is also applicable to study the shapes and changes in shape of particles.

It is thus seen that this invention provides a system for producing magnified images of particles such as aerosol droplets that are fed into a narrow sample zone and that the system is capable of displaying separate images of particles that exist there simultaneously and it is also clear that with this invention accurate measurements of individual particles droplets or other particles may be accurately measured, even though such particles are present simultaneously in the sample zone and with greatly reduced interference of light from out-of-focus particles at a distance from the focal plane.

The invention claimed is:

1. In apparatus for evaluating particles having a light transmitter for transmitting radiation as a beam along an optical axis to a sample zone; and optical means for transmitting radiation from an object plane in said sample zone along said optical axis and for focusing at a picture plane images of particles at said object plane said optical means rendering said object plane conjugate with respect to said picture plane, whereby images of particles simultaneously present at said object plane are sharply defined as separate images in said picture plane;

the improvement that comprises:

means for directing a stream of said particles into said sample zone along a path transverse to said optical axis whereby separate particles may be present there simultaneously; and wall means having apertures aligned with said optical axis on opposite sides of said sample zone for confining the flow of said stream to a narrow region at said object plane.

2. In an apparatus for evaluating particles, as defined in claim 1, means for displaying a visible areal image of the particle images formed in said picture plane.

3. In an apparatus for evaluating particles, as defined in claim 1, means for recording signals representative of an areal image formed in said picture plane.

4. In an apparatus for evaluating particles, as defined in claim 3, a viewing screen, means for reproducing on said viewing screen said signals as a visible areal image of the particle images formed in said picture plane, and means on said viewing screen for measuring the sizes of the particles imaged thereon 5. In apparatus for evaluating particles as defined in claim 1, wherein said light transmitter comprises means for supplying a collimated laser beam and a condensing lens for condensing said collimated laser beam at a focal area on the upbeam side of said object plane and adjacent said sample zone.

6. In apparatus for evaluating particles as defined in claim 1, wherein said light transmitter comprises means for supplying a laser beam to said sample zone, wherein said optical means comprises an apertured mirror for deflecting radiation from said sample zone to said picture plane, and means for imaging said laser beam at the aperture of said mirror to reduce the amount of the said beam that is not scattered by such particles from falling upon said picture plane.

7. In apparatus for evaluating particles as defined in claim 1, in which said wall means comprises first and second convex members having small coaxial apertures that provide said openings on opposite sides of said sample zone, the wall of said first convex member diverging away from said optical axis on the upbeam side of said sample zone and the wall of said second convex member diverging away from said optical axis on the downbeam side of said sample zone.

8. In apparatus for evaluating particles as defined in claim 1, in which said wall means comprises first and second cones arranged coaxially with said optical axis, said cones having said apertures at their tips and said cones being arranged with their apertured tips adjacent each other on opposite sides of said sample zone with the wall of said first cone diverging away from said optical axis on the upbeam side of said sample zone and with the wall of said second cone diverging away from said optical axis on the downbeam side of said sample zone.

9. In apparatus for evaluating particles as defined in claim 8, and comprising a tubular light-proof, gas-leak-proof tubular member embracing the space between said first cone and the space in which said collimated laser beam is transmitted, and a second light-proof, gas-leak-proof tubular member embracing the space between the second cone and said picture plane.

10. In apparatus for evaluating particles as defined in claim 7, comprising means for supplying gas under pressure to the space within said convex members and forcing air to flow gently into said sample zone while still permitting the stream of particles to flow through said sample zone from one side of said optical axis to the other.

11. In apparatus for evaluating particles as defined in claim 5, comprising means for adjusting the spacing of said condensing lens relative to said object plane along said optical axis.

12. In a method of evaluating particles, the steps that comprise:

establishing an optical axis;

establishing a sample zone at a position along said axis;

establishing an image plane that is transverse to said optical axis;

establishing in said sample zone an object plane that is transverse to said optical axis;

optically conjugating said object plane with respect to said image plane by positioning optical elements between said planes whereby particles at said object plane are brought to a sharp focus in said image plane;

transmitting a beam of radiation along said optical axis towards said sample zone;

directing a stream of said particles into said sample zone along a path transverse to said optical axis; and interposing on opposite sides of said sample zone two walls having openings therein with said optical axis passing through said openings, thereby restricting the direct flow of said stream to a narrow region that includes said object plane thereby largely confining the paths of travel of particles to a region approximating the depth of focus at the object plane, whereby the images of such particles are focused on said image plane with little interference from out-of-focus images of particles outside said narrow region and movement of particles out of said sample zone along said optical path is impeded;

whereby images of particles at said object plane are sharply defined in said image plane.

13. In a method of evaluating particles as defined in claim 12, including the steps of:

developing electric signals representative of the areal distribution of light in said image plane;

utilizing said electrical signals to form on a viewing screen, a visible image of the images formed in said image plane;

and the measuring sizes of particle images formed on said viewing screen.

14. In a method of evaluating particles as defined in claim 12, the steps that include:

positioning a photosensitive screen at said image plane;

reproducing the image formed at said screen as an optical image on a viewing screen thereby forming on said viewing screen an areal image of particles in said sample zone;

and measuring the dimensions of the particle images formed on said viewing screen to determine the sizes of said particles.

15. In apparatus for evaluating liquid aerosol particles suspended in air having a light transmitter for transmitting radiation as a beam along an optical axis to a sample zone and having optical means having optical surfaces for transmitting radiation from an object plane in said sample zone along said optical axis and for focusing images of particles in said object zone at a picture plane, said optical means rendering said object plane conjugate with respect to said picture plane, whereby images of particles in said object plane are sharply defined in said picture plane; the improvement comprising:

sample supply means for directing a stream of said particles into said sample zone along a path transverse to said optical axis; and means including wall members on opposite sides of said sample zone and having openings therein through which said optical axis passes for confining the flow of said stream to a narrow region at said object plane and for impeding the flow of aerosol particles toward said optical surface.

16. In apparatus for evaluating particles, as defined in claim 15;

means for recording signals representative of an areal image formed in said picture plane;

a viewing screen;

means for reproducing on said viewing screen said signals as a visible areal image of the particle images formed in said picture plane;

and means on said viewing screen for measuring the sizes of the particles imaged thereon.

17. In apparatus for evaluating particles as defined in claim 15, in which said sample supply means comprises first and second convex members having small coaxial apertures that provide such openings on opposite sides of said sample zone, the wall of said first convex member diverging away from said optical axis on the upbeam side of said sample zone and the wall of said second convex member diverging away from said optical axis on the downbeam side of said sample zone.

18. In apparatus for evaluating particles as defined in claim 17, comprising means for supplying gas under pressure forcing air to flow gently through said apertures into said sample zone from opposite sides thereof while still permitting the aerosol particles to flow to said sample zone.

19. In a method of evaluating aerosol particles suspended in air, the steps that comprise:

establishing an optical axis;

establishing a sample zone at a position along said axis;

establishing an image plane that is transverse to said optical axis;

establishing in said sample zone an object plane that is transverse to said optical axis;

optically conjugating said object plane with respect to said image plane by positioning optical elements between said planes whereby particles in said object plane are brought to a sharp focus in said image plane;

transmitting a beam of radiation along said optical axis towards said sample zone;

flowing air in which said aerosol particles are suspended to enter said sample zone along a path transverse to said optical axis;

interposing on opposite sides of said sample zone two walls having openings therein with said optical axis passing through said openings, thereby restricting the flow of said air to a narrow region on both sides of said object plane thereby largely concentrating such aerosol particles to a region approximating the depth of focus at the object plane, whereby the images of such particles are focused on said image plane with little interference from out-of-focus images of particles outside said narrow region;

whereby images of such aerosol particles in said object plane are sharply defined in said picture plane.

20. In a method for evaluating aerosol particles suspended in air as defined in claim 19, the additional step that comprises:

flowing gas gently through said openings into said sample zone from both sides thereof while still permitting air in which said aerosol particles are suspended to enter said sampld zone along a path transverse to said optical axis.

21. In a method for evaluating particles as defined in claim 12, the additional step that comprises:

forcing fluid gently through said openings into said sample zone from both sides thereof while still permitting said stream of particles to enter said sample zone along a path transverse to said optical axis.

* * * * *